United States Patent
Lippa et al.

(10) Patent No.: US 6,377,693 B1
(45) Date of Patent: Apr. 23, 2002

(54) TINNITUS MASKING USING ULTRASONIC SIGNALS

(75) Inventors: Arnold S. Lippa, Tucson; James A. Nunley, Scottsdale, both of AZ (US)

(73) Assignee: Hearing Innovations Incorporated, Tucson, AZ (US)

( * ) Notice: Subject to any disclaimer, the term of this patent is extended or adjusted under 35 U.S.C. 154(b) by 0 days.

(21) Appl. No.: 08/264,527

(22) Filed: Jun. 23, 1994

(51) Int. Cl.[7] .................. A61F 11/06; A61N 1/00
(52) U.S. Cl. ............. 381/71.6; 381/71.1; 607/136; 607/137
(58) Field of Search .............. 381/73.1, 83, 68.2, 381/68.4, 93; 607/55, 56, 136, 137; 601/2; 600/25, 28; 128/746

(56) References Cited

U.S. PATENT DOCUMENTS

| | | | | |
|---|---|---|---|---|
| 2,235,733 A | * | 3/1941 | Witting | 381/73.1 |
| 3,384,090 A | * | 5/1968 | Manfredi | 607/55 |
| 3,567,863 A | * | 3/1971 | Morrissey | 381/73.1 |
| 3,629,521 A | * | 12/1971 | Puharich et al. | 607/56 |
| 4,982,434 A | | 1/1991 | Lenhardt et al. | 381/68.3 |
| 5,285,499 A | * | 2/1994 | Shannon et al. | 381/68.3 |

FOREIGN PATENT DOCUMENTS

SU 000931191 A * 5/1982 .............. 601/2

OTHER PUBLICATIONS

Development of implanted electrical tinnitus suppressor; Matsushima ; Japanese Journal of Medical Electronics and Biological Eng. vol. 32 No. 1 p. 21–7 3–94 (Abstract Only).*

* cited by examiner

*Primary Examiner*—Jerome Grant, II
(74) *Attorney, Agent, or Firm*—Rothwell, Figg, Ernst & Manbeck

(57) ABSTRACT

A method and apparatus for treating tinnitus involves generating a noise signal to mask the ringing or buzzing in the ears caused by tinnitus and transposing the noise signal into the ultrasonic frequency range. As such, the masking signal effectively masks the tinnitus noise without interfering with the subject's perception of normal sounds such as human speech. In an alternative embodiment, human speech is transduced into electrical signals, transposed to the ultrasonic frequency range, and physically applied to the patient while tinnitus masking signals in the auditory range are applied to the patient.

12 Claims, 1 Drawing Sheet

TINNITUS MASKING USING ULTRASONIC SIGNALS

BACKGROUND OF THE INVENTION

The present invention relates generally to methods and apparatus for improving the hearing sensory response of human subjects and more specifically relates to methods and apparatus for treating the symptoms of tinnitus.

Tinnitus is an affliction of the human sensory system which causes a persistent buzzing, ringing or whistling sound in the ears or head. One possible cause of tinnitus is a defect in the auditory nerve, although all possible causes of tinnitus are not fully known.

In an effort to relieve the annoyance caused by tinnitus, one known treatment is to apply variable preferred bands of white noise to the patient in the auditory range, which serves to mask the tinnitus ringing or buzzing. However, this treatment is usually unsatisfactory because the masking noise can interfere with the patient's normal hearing perception.

Therefore, there exists in the art a need for an effective treatment for the symptoms of tinnitus without degrading a patient's perception of ordinary sounds such as speech.

SUMMARY OF THE INVENTION

The present invention overcomes the deficiencies in the prior art by providing a method and apparatus for masking tinnitus through the use of ultrasonic frequency signals. In one embodiment of the invention, masking stimuli in the ultrasonic range are applied to the body to mask the tinnitus symptoms. In another embodiment of the invention, human speech is transposed into the ultrasonic range and applied to the body, while masking stimuli in the auditory range are applied to the patient in a conventional manner.

In particular, the present invention provides apparatus for treating a patient for symptoms caused by tinnitus, comprising means for generating a masking noise signal in an ultrasonic frequency range, and means for applying said masking noise signal physically to a selected body part of said patient. The present invention further provides a method for treating a patient for symptoms of tinnitus, comprising the steps of generating a masking noise signal in an ultrasonic frequency range, converting said masking noise signal into a human sensory signal, and applying said sensory signal to a selected body part of said patient.

Lenhardt et al. U.S. Pat. No. 4,982,434 discloses a hearing aid system which shifts sound signals from the auditory range to the ultrasonic frequency range (referred to in the patent as "supersonic" frequencies) and applies the ultrasonic signals to the human sensory system through bone conduction. The Lenhardt et al. patent is incorporated herein in its entirety.

BRIEF DESCRIPTION OF THE DRAWINGS

The present invention will become more fully understood from the detailed description given hereinbelow and the accompanying drawings, which are given for purposes of illustration only and are not limitative of the present invention, and wherein.

DETAILED DESCRIPTION OF THE PREFERRED EMBODIMENTS

Figure 1:
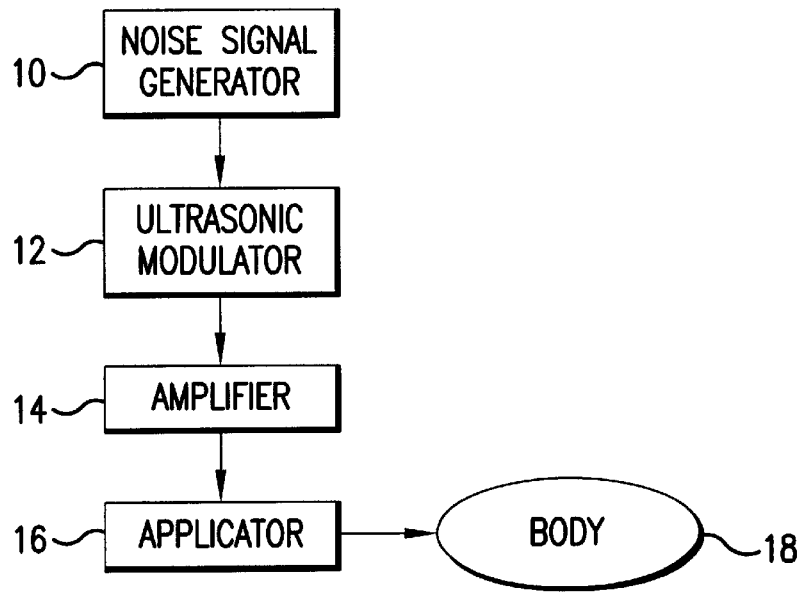
FIG. 1 is a block diagram of a first preferred embodiment of the present invention.

The present invention will now be described in detail with reference to FIGS. 1 and 2. A first preferred embodiment of the present invention is shown in FIG. 1. A noise signal generator 10 develops signals which provide sensory stimuli in the auditory range when applied to an appropriate transducer (or applicator as referred to hereinafter). The signals developed by the signal generator 10 may include, but are not restricted to, sine waves, square waves, white noise, or clicks. These various signals are generically referred to as "noise" hereinafter. The signals from the generator 10 are selected for minimum perception by the patient while still effective in masking tinnitus.

The signals from the generator 10 are inputted to an ultrasonic modulator 12 wherein they are transposed into the ultrasonic frequency range, which is above 20,000 hertz and extends to approximately the 100,000 hertz range. In particular, an ultrasonic carrier of 25,000 to 30,000 hertz has been found to work well. As an alternative to the apparatus of FIG. 1, the signals from the noise signal generator may originate in the ultrasonic frequency range in which case an ultrasonic modulator would not be needed. The ultrasonic noise signals are inputted to an amplifier 14 for suitably increasing the amplitude of the signal. The volume and frequency of the ultrasonic masking signals are adjusted for optimum efficacy in masking tinnitus.

The amplified signal from the amplifier 14 is inputted to an applicator 16 for application to the body 18. Applicator 16 may be an electric/vibratory transducer such as a piezo-electric driver attached to the skull for bone conduction, or it may in the form of a speaker which creates physical vibrations in the air, which vibrations are transmitted in wave form through the air to physically impact a predetermined portion of the body which is responsive to physically applied vibrations for creating a perception in the brain. Additionally, the applicator 16 may be an electrode which directly applies an electromagnetic signal to a selected portion of the body.

The ultrasonic stimuli (above 20 kHz) perceived by the brain have been clinically shown to be effective in masking the ringing or buzzing in the ears associated with tinnitus, while not interfering with the perception of speech or other normal sounds.

Figure 2:
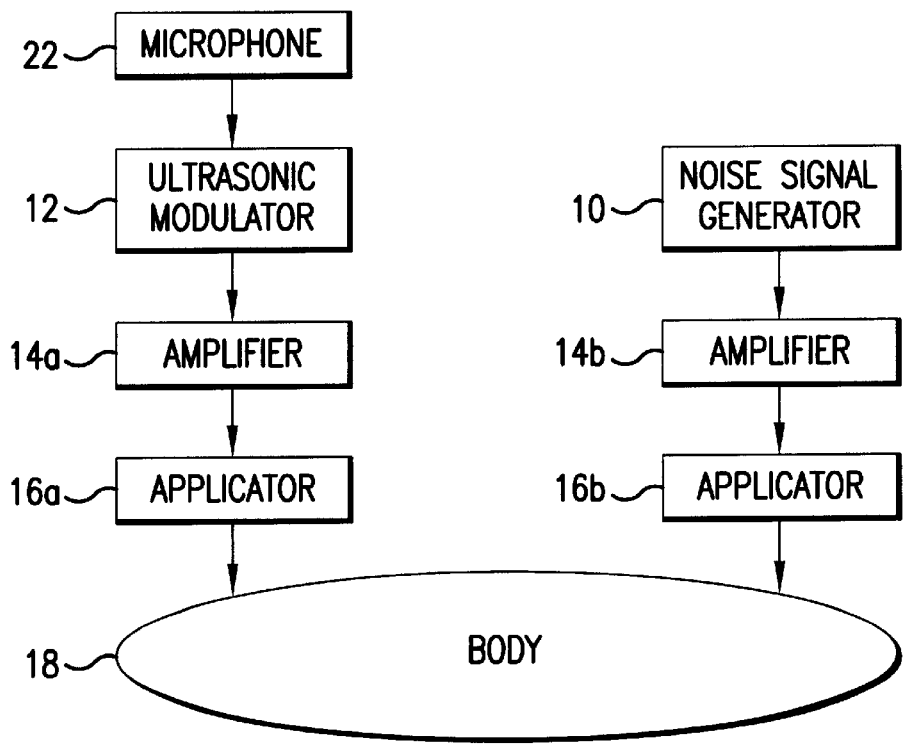
FIG. 2 is a block diagram of an alternative preferred embodiment of the present invention.

An alternative embodiment is shown in FIG. 2 in which like reference numerals are used to denote like elements in FIG. 1. In this embodiment, a microphone 22 is used to pick up auditory stimuli from the environment, such as human speech, and convert it into an electrical input signal for transposition to the ultrasonic frequency range. As taught by the Lenhardt et al. patent, sound in the normal auditory frequency range can be perceived by the brain when it is transposed to the ultrasonic range and applied vibrationally to the body, such as by bone conduction, for example. This ultrasonic signal is resistant to masking by stimuli in the auditory frequency range (i.e., 100 to 20,000 hertz). In this embodiment, auditory frequency masking stimuli are generated by signal generator 10, and applied to the body via amplifier 14b and applicator 16b, which may be in the form of headphones or a vibrational transducer. Speech is transposed from the auditory frequency range by ultrasonic modulator 12 and applied to the body vibrationally via amplifier 14a and applicator 16a. This embodiment may be especially useful for tinnitus sufferers who are hearing impaired.

The invention having been thus described, it will be apparent to those skilled in the art that the same may be varied in many ways without departing from the spirit and scope of the invention. Any and all such modifications are intended to be covered by the following claims.

What is claimed is:

1. Apparatus for treating a patient for symptoms caused by tinnitus, comprising:

means for generating a masking noise signal in an ultrasonic frequency range; and an electric/vibratory transducer for applying said masking noise signal physically to a selected body part of said patient to alleviate said symptoms caused by tinnitus.

2. Apparatus for treating a patient for symptoms caused by tinnitus, comprising:

means for generating a masking noise signal in an ultrasonic frequency range; and means for applying said masking noise signal physically to a selected body part of said patient to alleviate said symptoms caused by tinnitus;

wherein said generating means comprises a noise signal generator which generates an auditory masking noise signal in an auditory frequency range, and an ultrasonic modulator for transposing said auditory masking noise signal to said ultrasonic frequency range.

3. Apparatus according to claim 2, wherein said auditory masking noise signal is a white noise signal.

4. Apparatus according to claim 2, wherein said auditory masking noise signal is a sine wave signal.

5. Apparatus according to claim 2, wherein said auditory masking noise signal is a square wave signal.

6. Apparatus for treating a patient for symptoms of tinnitus, comprising:

means for generating a masking noise signal in an auditory frequency range;

means for applying said masking noise signal to a selected body part of said patient to alleviate said symptoms of tinnitus;

transducer means for converting sounds in an auditory frequency range into audio frequency electrical signals;

ultrasonic modulator means for converting said audio frequency electrical signals into ultrasonic frequency electrical signals; and means for applying said ultrasonic frequency electrical signals physically to a selected body part of said patient.

7. A method for treating a patient for symptoms of tinnitus, comprising the steps of:

generating a masking noise signal in an ultrasonic frequency range;

converting said masking noise signal into a vibratory signal; and applying said vibratory signal to a selected body part of said patient to alleviate said symptoms of tinnitus.

8. A method according to claim 7, wherein said generating step comprises the steps of generating a first audio frequency masking signal and transposing said first audio frequency masking signal to an ultrasonic frequency range to attain said masking noise signal.

9. Apparatus for treating a patient for symptoms caused by tinnitus, comprising:

a noise signal generator for generating a masking noise signal in an ultrasonic frequency range; and means for applying said masking noise signal physically to a selected body part of said patient to alleviate said symptoms caused by tinnitus.

10. Apparatus according to claim 9, wherein said auditory masking noise signal is a white noise signal.

11. Apparatus according to claim 9, wherein said auditory masking noise signal is a sine wave signal.

12. Apparatus according to claim 9, wherein said auditory masking noise signal is a square wave signal.

* * * * *